(12) United States Patent
Udengaard et al.

(10) Patent No.: US 11,246,766 B2
(45) Date of Patent: Feb. 15, 2022

(54) HIGH BARRIER NONWOVEN FABRIC

(71) Applicant: FIBERTEX PERSONAL CARE A/S, Aalborg Ost (DK)

(72) Inventors: Brian Udengaard, Lystrup (DK); Barbara Harling Hede, Aalborg (DK); Thomas Broch, Gistrup (DK)

(73) Assignee: FIBERTEX PERSONAL CARE A/S, Aalborg Ost (DK)

( * ) Notice: Subject to any disclaimer, the term of this patent is extended or adjusted under 35 U.S.C. 154(b) by 676 days.

(21) Appl. No.: 16/081,809

(22) PCT Filed: Dec. 5, 2016

(86) PCT No.: PCT/EP2016/002039
§ 371 (c)(1),
(2) Date: Aug. 31, 2018

(87) PCT Pub. No.: WO2017/152925
PCT Pub. Date: Sep. 14, 2017

(65) Prior Publication Data
US 2019/0070045 A1    Mar. 7, 2019

(30) Foreign Application Priority Data

Mar. 9, 2016 (EP) ..................... 16159433

(51) Int. Cl.
*D04H 3/12* (2006.01)
*A61F 13/475* (2006.01)
(Continued)

(52) U.S. Cl.
CPC ............ *A61F 13/475* (2013.01); *D01D 5/34* (2013.01); *D01F 1/10* (2013.01); *D01F 6/06* (2013.01);
(Continued)

(58) Field of Classification Search
None
See application file for complete search history.

(56) References Cited

U.S. PATENT DOCUMENTS 8,470,222 B2    6/2013 Shi et al.
2005/0182198 A1    8/2005 Cheng et al.
(Continued)

FOREIGN PATENT DOCUMENTS

EP    2270271 A1    1/2011
EP    2778270 A1    9/2014
(Continued)

OTHER PUBLICATIONS

Gakkai-Hen, S., "Sen-i Binran Kako-hen," Maruzen, 2nd Edition, Mar. 24, 1994, 4 pages. (See NPL 2, Japanese Office Action Issued in Application No. 2018-548454 for Explanation of Relevance).

(Continued)

*Primary Examiner* — Monica A Huson
*Assistant Examiner* — Kelsey C Grace
(74) *Attorney, Agent, or Firm* — McCoy Russell LLP

(57) ABSTRACT

The invention relates to a method for making a nonwoven fabric comprising forming polymer fibers from a melt of the polymer material and using these fibers to obtain a nonwoven fabric during a subsequent nonwoven fabric formation procedure, wherein the melt of the polymer material comprises a melt additive, wherein the method comprises thermal bonding at a temperature higher than 40° C. below the melting point of the polymer material and, additionally, one or both of the following steps: a. improving the mobility of the additive by heat-treating the nonwoven fabric at 100° C. or more for 0.1 seconds or more after the nonwoven fabric formation procedure and/or including a filler having a higher thermal conductivity than the polymer material to the polymer material; b. influencing the polymer crystallinity by (Continued)

Figure 1:
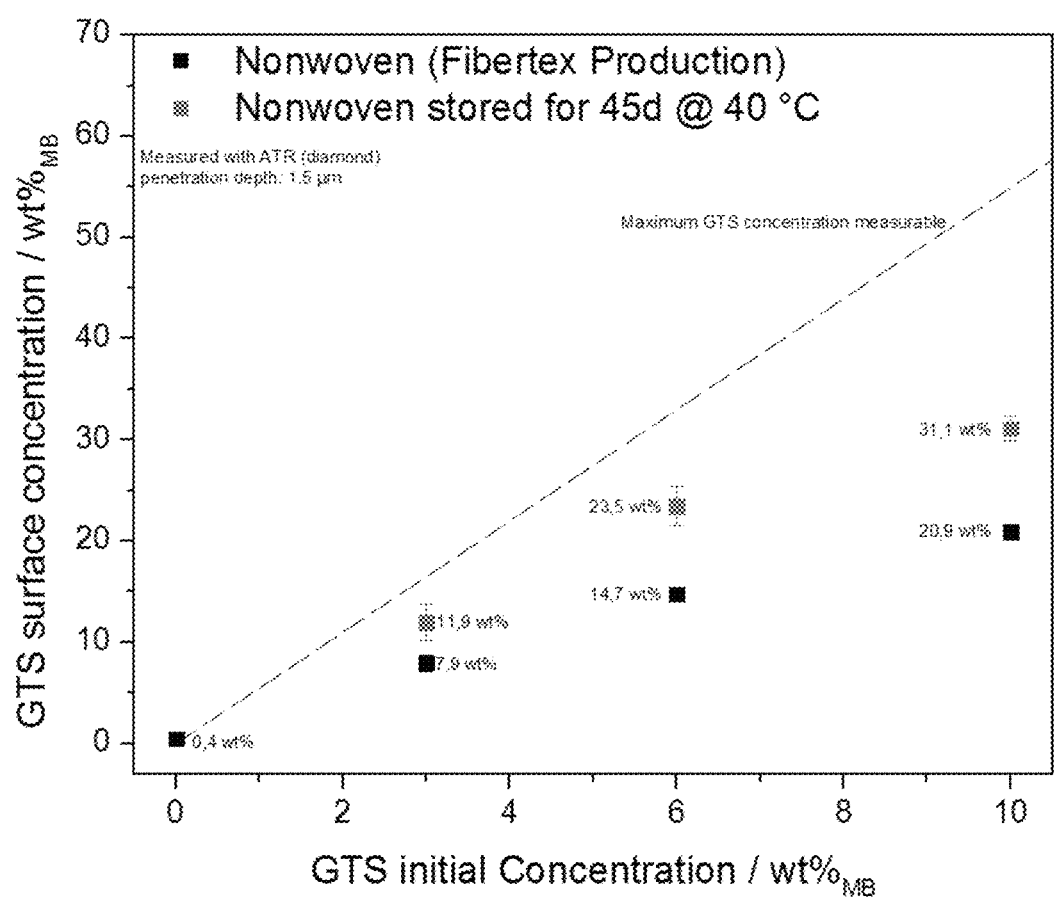
Figure 2:
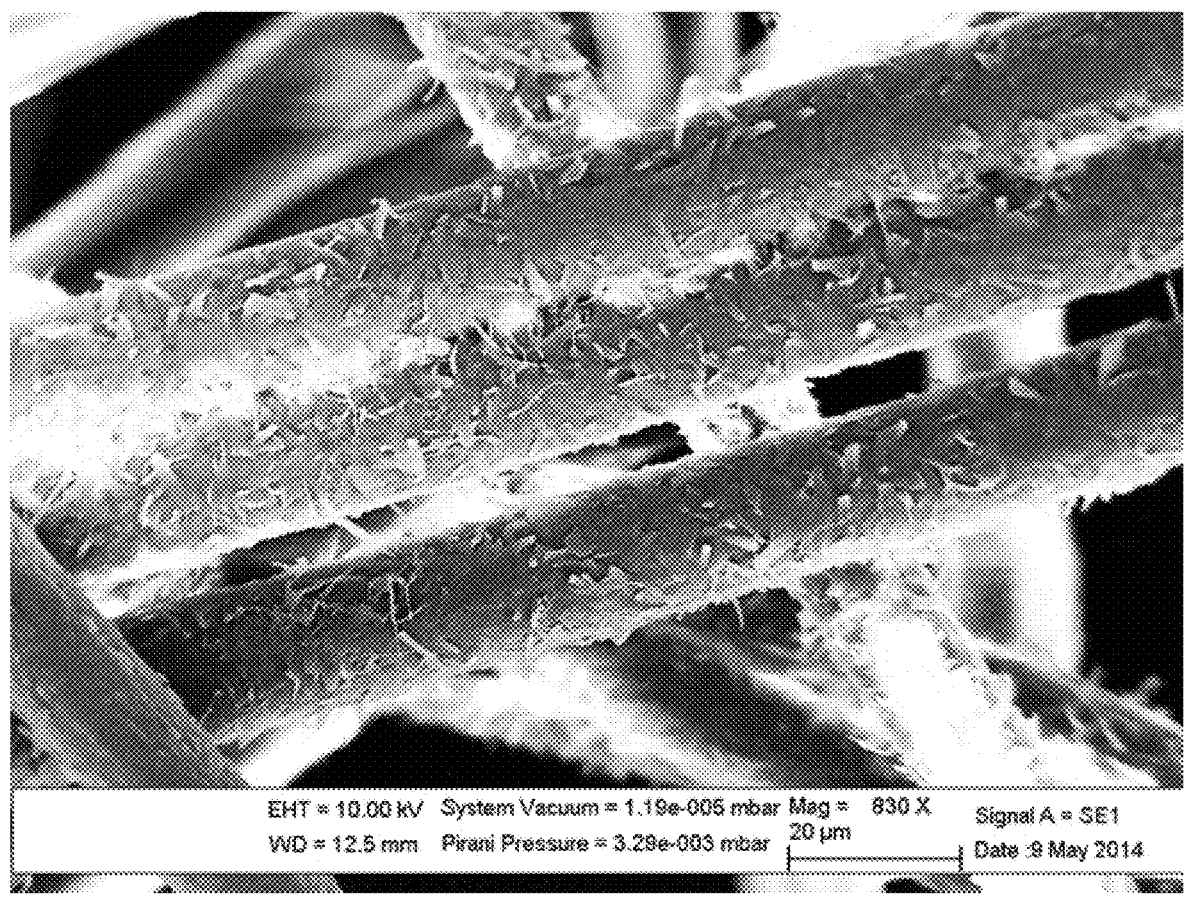
Figure 3:
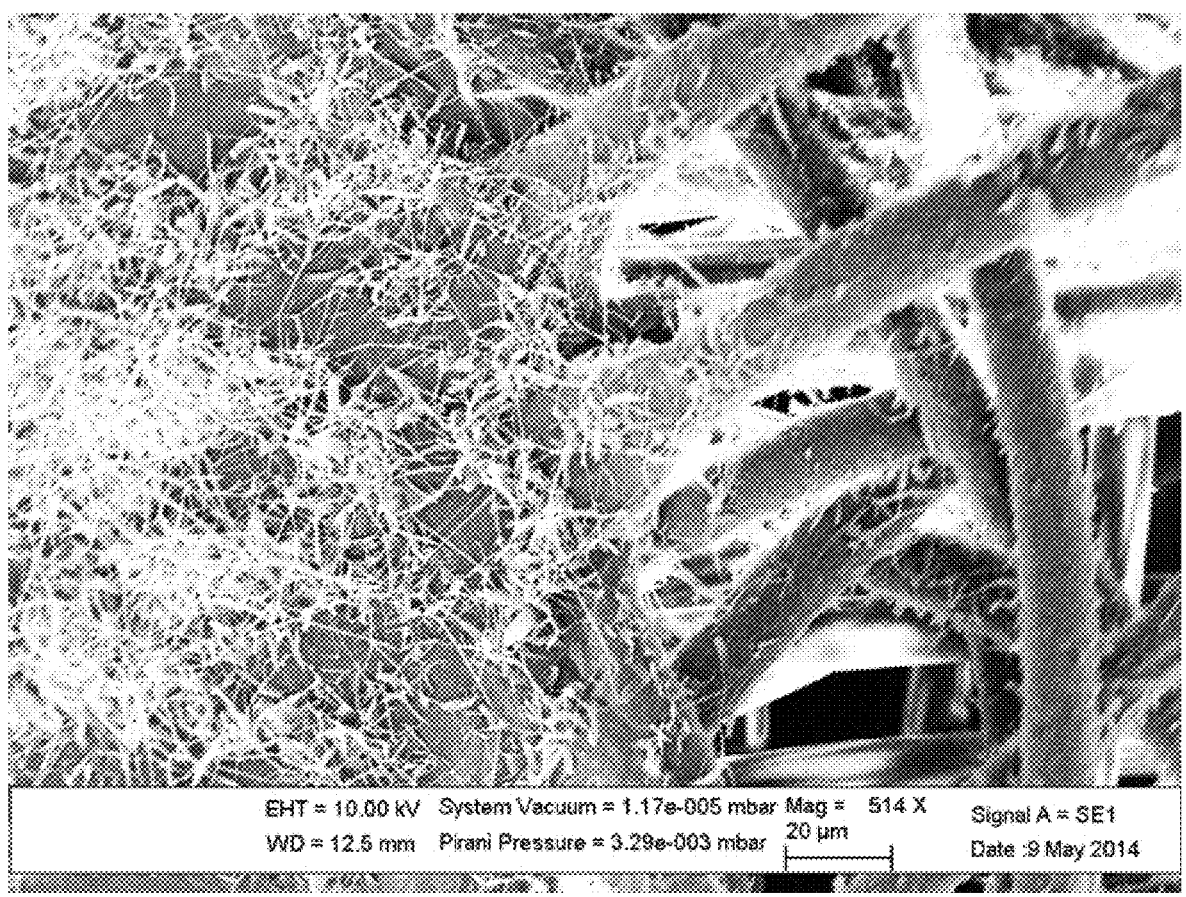

including a nucleating agent, branched polymers and/or random co-polymers to the polymer material.

20 Claims, 3 Drawing Sheets

(51) Int. Cl.
| | |
|---|---|
| D04H 1/4291 | (2012.01) |
| D04H 1/544 | (2012.01) |
| D04H 1/552 | (2012.01) |
| D04H 3/007 | (2012.01) |
| D04H 3/16 | (2006.01) |
| D01D 5/34 | (2006.01) |
| D01F 1/10 | (2006.01) |
| D04H 1/54 | (2012.01) |
| D04H 3/14 | (2012.01) |
| D04H 1/541 | (2012.01) |
| D04H 1/56 | (2006.01) |
| D01F 6/06 | (2006.01) |
| D01F 6/04 | (2006.01) |

(52) U.S. Cl.
CPC .............. *D04H 1/4291* (2013.01); *D04H 1/54* (2013.01); *D04H 1/544* (2013.01); *D04H 1/5412* (2020.05); *D04H 1/552* (2013.01); *D04H 1/565* (2013.01); *D04H 3/007* (2013.01); *D04H 3/12* (2013.01); *D04H 3/14* (2013.01); *D04H 3/16* (2013.01); *D01F 6/04* (2013.01)

(56) References Cited

U.S. PATENT DOCUMENTS

| | | |
|---|---|---|
| 2012/0088424 A1 | 4/2012 | Eric et al. |
| 2012/0237718 A1* | 9/2012 | Weisman ............... D04H 3/011 428/89 |
| 2014/0070443 A1 | 3/2014 | McAmish et al. |

FOREIGN PATENT DOCUMENTS

| | | |
|---|---|---|
| JP | 2010529309 A | 8/2010 |
| JP | 2014181436 A1 | 9/2014 |
| WO | 9850611 A1 | 11/1998 |
| WO | 0006817 A1 | 2/2000 |
| WO | 2012014769 A1 | 2/2012 |

OTHER PUBLICATIONS

Japanese Patent Office, Office Action Issued in Application No. 2018-548454, dated Oct. 13, 2020, 13 pages.

ISA European Patent Office, International Search Report Issued in Application No. PCT/EP2016/002039, dated Mar. 13, 2017, WIPO, 3 pages.

European Patent Office, Extended European Search Report Issued in Application No. 17159541.6, dated Jul. 10, 2017, Germany, 9 pages.

\* cited by examiner

HIGH BARRIER NONWOVEN FABRIC

CROSS-REFERENCE TO RELATED APPLICATION

The present application is a U.S. National Phase of International Patent Application Serial No. PCT/EP2016/002039, entitled "HIGH BARRIER NONWOVEN FABRIC," filed on Dec. 5, 2016. International Patent Application Serial No. PCT/EP2016/002039 claims priority to European Patent Application No. 16159433.8, filed on Mar. 9, 2016. The entire contents of each of the abovementioned applications are hereby incorporated by reference in their entirety for all purposes.

TECHNICAL FIELD

The invention relates to methods for making nonwoven fabrics comprising polymer fibers whose surface properties are modified upon including an additive to the polymer matrix. For example, the hydrophobic and oleophobic character of the fiber surface can be modified for improved barrier properties of the nonwoven, which can be desirable in the hygiene industry. The invention further relates to nonwoven fabrics obtainable by such methods.

BACKGROUND AND SUMMARY

In the past there were numerous approaches to increase the liquid barrier properties of a nonwoven including, to only name a few, increasing the basis weight of the nonwoven, increasing the content of thinner meltblown fibers in a spunmelt fabric or coating of the fibers.

EP 2 270 271 B1 discloses that adding lipid esters as melt additives to the polymer matrix of the fibers leads to increased barrier properties in a nonwoven fabric. EP 2 778 270 A1 describes that the increased barrier properties may be connected to a specific surface topography of the fibers, which can be obtained by including said melt additives. WO 00/06817 A1 uses in-line hot air knives to increase barrier properties by additive migration in certain regions of a fabric.

The present invention aims to obtain improved results in surface property modification at lower melt additive concentration.

Against this background, the invention relates to a method for making a nonwoven fabric comprising forming polymer fibers from a melt of the polymer material and using these fibers to obtain a nonwoven fabric during a subsequent nonwoven fabric formation procedure, wherein the melt of the polymer material comprises a melt additive, the method comprising thermal bonding at a temperature higher than 40° C. below the melting point of the polymer material and, additionally, one or both of the following steps to increase the relative concentration of the melt additive in the surface region of the fibers: a. improving the mobility of the additive by heat-treating the nonwoven fabric at 100° C. or more for 0.1 seconds or more after the nonwoven fabric formation procedure and/or including a filler having a higher thermal conductivity than the polymer material to the polymer material; b. influencing the polymer crystallinity by including a nucleating agent, branched polymers and/or random co-polymers to the polymer material.

The invention is based on the theory that fiber surface properties in general and fiber surface structure formation in particular are connected to the additive concentration at the surface. It is further based on the theory that some small molecular additives tend to travel to the surface of the fibers if allowed to migrate within the polymer matrix. The steps proposed by the invention to increase the relative concentration of the additive in the surface region of the fibers correspond to two basic approaches which take account of these theoretical considerations. One of these basic approaches is to increase mobility of the polymer matrix and hence the speed the additive can migrate. The other of these basic approaches is to decrease the distance the additive has to travel to reach the surface by changing the crystallinity.

In one embodiment, bonding at a temperature higher than 40° C. below the melting point of the polymer material can be carried out by calandering or hot air through bonding.

In one embodiment, the polymer material consists of or comprises a thermoplastic polymer. It may consist of or comprise a polyolefin such as polypropylene and/or polyethylene and/or Ethylene-Propylene copolymer or a combination of either of these.

Heat treatment after the nonwoven formation procedure means that heat is applied in addition to the heat already applied as per normal production (e.g., during pre-compaction and bonding). It pertains to heat-treatment after the nonwoven has been bonded. This can be achieved by increasing the temperature in the processing of the formed nonwoven fabric (by applying one or several inline heat activation steps) and/or by post-activation when converting the nonwoven into its final application. Generally, heat-treatment after the nonwoven formation procedure refers to heating the nonwoven to temperatures above 100° C., but could also refer to an increased storage temperature of the nonwoven at 30° C., 35° C. or 40° C. In some embodiments described in the following, higher temperatures are used. Such heat treatment promotes the mobility of the additive and hence its migration to the surface after the nonwoven fabric has been formed. The heat activation can both directly affect the movement speed of the additive as well as indirectly, by making the polymeric matrix easier to move in for the additive. Heat activation already occurs during in-line thermal bonding, e.g., calander bonding, through-air bonding, ultra sonic bonding and/or radiant heat bonding. According to the invention, additional heat treatments, e.g., application of a drying oven, IR radiation, hot air knives or ultra sonic heating, are applied after the nonwoven formation procedure. They can be in-line and applied to the finished and finally bonded nonwoven, but could also be off-line, or both. It could be heat treatment after the nonwoven has been cut. For example, heat activation after the nonwoven formation procedure can comprise storing the nonwoven at increased temperatures, e.g., at more than 30 or 40° C., for an extended amount of time, e.g., 12 or 24 hours or more. Also, a shorter treatment (e.g., 5 seconds or 0.1 seconds or less) at a temperature of more than 80° C., 100° C., 120° C. or 135° C. may be suitable employed. The additional heat activation of the invention, in-line and/or off-line, can be in the full web area, but could also be in specific zones only. In one embodiment, heat-treating after the nonwoven fabric formation procedure includes storing the nonwoven at 30° C. or more for 12 hours or more or at 100° C. or more for 15 minutes or less.

In one embodiment, fillers having a higher thermal conductivity than the polymer material are included to the polymer material. Exemplary fillers include inorganic fillers such as calcium carbonate, which can have a higher thermal conductivity than the polymer matrix (e.g., than polypropylene), allowing faster and more homogeneous transfer of heat within the fiber matrix. This will allow for more benefit from the heat already applied in the processing of the nonwoven and, if any, may increase the effect of heat treatment after the nonwoven formation procedure. The particle size of the filler may be important for the observed effect. In one embodiment, the average particle size of the filler is hence 10 μm or smaller, preferably 1 μm or smaller (ISO 14688). The material may also be chosen to exhibit a thermal conductivity at room temperature of 1 W·m−1·K−1 or greater or more, preferably 2.0 W·m−1·K−1 or more (DIN EN 12664). A preferred thermal conductivity could be 2.7 W·m−1·K−1, which approximately corresponds to that of CaCO3. In one embodiment, the filler comprises CaCO3. Suitable CaCO3 can in one example be either ground CaCO3 (GCC) or precipitated CaCO3, or a combination thereof. For example, the CaCO3 can be micro-CaCO3 (GCC) having a Plus 325 Mesh of 0.002% and/or mean particle size of 1.6 microns and/or specific surface area of 4.5 m2/g. Such material is, for example, contained in a masterbatch under the trade name "Fiberlink 201S" from A. Schulman. In another example, the CaCO3 can be nano-CaCO3 (PCC) having a residue on sieve 45 micron <250 ppm and/or mean particle diameter of 0.07-0.13 microns and/or specific surface area 16 m2/g. Such material is, for example, found under the tradename SOCAL® U1S2 from Imerys Group.

Step b. is concerned with changing the morphology of the polymeric matrix and hence the distance the melt additive has to navigate when traveling through the matrix.

A nucleating agent increases the number of sites where crystallites begin to form, thereby decreasing the area the crystallites have to grow before they will impinge on each other. Hereby the crystallites will be dimensionally smaller and the additive will have a shorter distance to travel before it reaches the fiber surface. In general melt additives are only able to migrate through the amorphous domains of the polymeric matrix at room temperature, but dependent on the degree of crystallinity (or degree of amorphousness), the geometry and size of the amorphous regions, as well as the conformation and size of the migratory additive, the additive may not be able to migrate effectively at all, as it can be too constricted to move. Therefore, once the processing of the nonwoven is complete, the less constricted the path composed of the amorphous phase, the more additive will be able to reach the surface before the polymer has recrystallized. Suitable nucleating agents can be both inorganic or organic, and insoluble and soluble in the polymer matrix. In one embodiment, the nucleating agent comprises a nonitol, trisamide and/or a sorbitol based nucleating agent. Nonitol can be obtained, for example, from Millad® NX™ 8000 or any masterbatches containing that active component, e.g. NX™ UltraClear GP 110B. Trisamide can be obtained, for example, from Irgaclear XT 386 or any masterbatches containing that active component. A sorbitol based nucleating agent can be obtained, for example, from NC 4 from Mitsui Chemicals.

In one embodiment, an inorganic particulate such as, for example, CaCO3, the inorganic particulate having a particle size of 10 μm or smaller and preferably 1 μm or smaller can be used as a nucleating agent. It has been found out that inorganic particulate can act as both nucleating agent for influencing polymer crystallinity as well as means for improving heat conduction and hence improving additive mobility. In this respect, it is observed that the improvement of heat conduction appears to be the predominant factor to influence additive migration.

Including branched polymers and/or random co-polymers to the polymer material may result in a polymeric matrix that inherently allows the additive to move more freely and less constricted and therefore faster. Diffusivity may be promoted, e.g., by using/adding branched polymers or random-copolymers as/to the polymer material. If branched polymers and/or random co-polymers are added to the polymer material, the indication of thermal bonding at a temperature higher than 40° C. below the melting point of the polymer material refers to the melting point of the mixture.

In one embodiment, multicomponent and in particular bicomponent technology is used and the additive added to only (or predominantly) the polymer feeds eventually forming at least the predominant part of the outermost area of the fibers. The bicomponent could be of core-sheath, but is not limited thereto, and can also be island-in-the-sea, side-by-side, etc. configuration allowing the additive to be added to the surface part of a given bicomponent, e.g. the sheath of the core/sheath bicomponent configuration. Also apart from the additive, the polymeric components of the multicomponent fiber do not have to be identical. In one embodiment, different polymers matrices are employed for the two feeds. The matrix including the additive could also make use of any other measure envisioned in steps a. and b. In one embodiment, the one and the other polymer material both are made of or comprise a thermoplastic polymer, preferably a polyolefin such as polypropylene and/or polyethylene and/or Ethylene-Propylene copolymer or a combination of either of these.

Of course, one or more of the steps and measures mentioned may be employed. For example, heat-treating after the nonwoven fabric formation procedure and including fillers may be used in conjunction. As another example, one or both of the measures for improving the mobility may be used in conjunction with either measure to influence the polymer crystallinity. This has shown to obtain very desirable effects.

Also other steps can be taken in conjunction with the steps and measures mentioned. Among these other steps are spinning thinner fibers, hereby decreasing the distance from the core to the surface. This could be done, but is not limited to, increasing the MFR of the polymer and/or increasing the stress on the fibers during spinning. It is obvious to the one knowledgeable in the state of the art that the migration of a migrating additive is faster/more efficient in a thinner fiber due to the shorter distance to traverse, i.e. the speed will be higher in a fiber with a diameter of 10 micron than in one with a diameter of 20 micron. The stress on fibers during spinning may also be responsible for different extents of stress induced crystallization. Also among these steps are changing the morphology of the polymeric matrix by changing the heating/cooling conditions while processing. As to, for example, the speed of cooling, super cooling is believed to be able to lock the migratory additive in the (amorphous) polymeric matrix. The type of the polymer (homo, co, random, block etc.) and the molecular weight of the polymer may also have an influence on morphology, in addition to the effects rendered with regard to item b.

In one embodiment, the method comprises a continuous process for making a nonwoven fabric, where the fibers are continuously spun and directly dispersed on a carrier belt, preferably comprises making a spunbonded and/or melt-blown nonwoven fabric.

In one embodiment, the nonwoven formation procedure includes bonding of the nonwoven fibers. Bonding may, for example, include calendaring and/or air-through bonding. Using a thermal bonding procedure can be advantageous as it already acts as primary heat activation during the nonwoven formation procedure.

In one embodiment, the additive comprises a hydrophobic molecule, preferably a hydrophobic molecule comprising a hydrocarbon chain of between 8-25 carbon atoms. In a preferred embodiment, the additive comprises a fatty acid ester derived from C8-25, C10-20 or C14-18 saturated or unsaturated carboxylic acids. Examples comprise oleic acid, palmitic acid, myristic acid, myristoleic acid, oleic acid, limoleic acid, linoleic acid and arachidonic acid. The fatty acid ester may be a triglyceride such as, for example, glycerol tristearate.

In one embodiment, the melt additive may be present in an amount of greater 1.2 wt % or greater 2 wt % based on the total weight of the polymer component. In one embodiment, the melt additive may be present in an amount of smaller 8 wt % or smaller 6 wt % based on the total weight of the polymer component. For multicomponent fibers, the component containing the additive may in one embodiment comprise higher additive contents. For example, contents of between 4-16 wt % are contemplated.

The invention further relates to a nonwoven fabric obtainable by the process of the invention. Such fabric comprises polymer fibers where the melt additive is included in the polymer matrix, where the concentration of the melt additive is higher in a surface region than in a core region of the fibers and wherein the fibers comprise a rugged surface topography.

In one embodiment, the surface comprises annexes such as fibrils, platelets or flakes that extend outwardly from the surface of the fibers. Fibrils include shapes such as elongate projections and bumps.

The average radial elevation of the annexes from the surface may be in the range of 5 nm-50 μm, preferably 100 nm-30 μm and more preferably 500 nm-20 μm.

In one embodiment, the nonwoven fabric comprises at least one spunbonded (S) layer which is obtained using the fibers from the additive-comprising melt of the polymer material.

In one embodiment, the nonwoven fabric comprises at least one meltblown (M) layer which is obtained using the fibers from the additive-comprising melt of the polymer material.

In one embodiment, the nonwoven fabric is a spunmelt and preferably a layered SMS-type fabric wherein fibers of at least one of the S and/or M layers are obtained using the fibers from the additive-comprising melt of the polymer material.

The nonwoven fabric according to the invention may be used, for example, in a disposable hygiene article such as baby diapers, feminine hygiene products, wipes or adult incontinence products. Within these articles and products, the nonwoven can be utilized for both barrier performance application, e.g. barrier leg cuff in a diaper context, but also converted to act as a masking product, e.g. in a topsheet/core wrap application in feminine hygiene products. Some steps of the present invention such as post production heat activation could be applied to selected zones of benefit to the target application.

Further details and advantages of the invention are hereinafter described with reference to examples.

When reference is made to a hydrophobic melt additive, more specifically PPM17000 High Load Hydrophobic, this refers to a masterbatch with an active component comprising 40 wt %.

When reference is made herein to Low Surface Tension Strike Through (LST-ST), it will be determined according to the following method.

The surface tension of a liquid is determined by measuring the force exerted on a platinum Wilhelmy plate at the air-liquid interface. A Kruss tensiometer K11 or equivalent is used. (Available by Kruss USA.) The test is operated in a laboratory environment at 23±2° C. and 50±5% relative humidity. The test liquid is placed into the container given by the manufacturer and the surface tension is recorded by the instrument and its software.

The low surface tension fluid strikethrough time test is used to determine the amount of time it takes a specified quantity of a low surface tension fluid, discharged at a prescribed rate, to fully penetrate a sample of a web (and other comparable barrier materials) which is placed on a reference absorbent pad. As a default, this is also called the 32 mN/m Low Surface Tension Fluid Strikethrough Test because of the surface tension of the test fluid and each test is done on two layers of the nonwoven sample simply laid on top of each other.

For the test, the reference absorbent pad is 5 plies of Ahlstrom grade 989 filter paper (10 cm×10 cm) and the test fluid is a 32 mN/m low surface tension fluid.

The test is designed to characterize the low surface tension fluid strikethrough performance (in seconds) of webs intended to provide a barrier to low surface tension fluids, such as runny BM, for example.

Lister Strikethrough Tester: The instrumentation is like described in EDANA ERT 153.0-02 section 6 with the following exception: the strike-through plate has a star-shaped orifice of 3 slots angled at 60 degrees with the narrow slots having a 10.0 mm length and a 1.2 mm slot width. This equipment is available from Lenzing Instruments (Austria) and from W. Fritz Metzger Corp (USA). The unit needs to be set up such that it does not time out after 100 seconds.

Reference Absorbent Pad: Ahlstrom Grade 989 filter paper, in 10 cm×10 cm areas, is used. The average strikethrough time is 3.3+0.5 seconds for 5 plies of filter paper using the 32 mN/m test fluid and without the web sample. The filter paper may be purchased from Empirical Manufacturing Company, Inc. (USA).

Test Fluid: The 32 mN/m surface tension fluid is prepared with distilled water and 0.42+/−0.001 g/liter Triton-X 100. All fluids are kept at ambient conditions.

Electrode-Rinsing Liquid: 0.9% sodium chloride (CAS 7647-14-5) aqueous solution (9 g NaCl per 1 L of distilled water) is used.

Test Procedure:

Ensure that the surface tension is 32 mN/m+/−1 mN/m. Otherwise remake the test fluid.

Prepare the 0.9% NaCl aqueous electrode rinsing liquid.

Ensure that the strikethrough target (3.3+/−0.5 seconds) for the Reference Absorbent Pad is met by testing 5 plies with the 32 mN/m test fluid as follows:

Neatly stack 5 plies of the Reference Absorbent Pad onto the base plate of the strikethrough tester.

Place the strikethrough plate over the 5 plies and ensure that the center of the plate is over the center of the paper. Center this assembly under the dispensing funnel.

Ensure that the upper assembly of the strikethrough tester is lowered to the pre-set stop point.

Ensure that the electrodes are connected to the timer.

Turn the strikethrough tester "on" and zero the timer.

Using the 5 mL fixed volume pipette and tip, dispense 5 mL of the 32 mN/m test fluid into the funnel.

Open the magnetic valve of the funnel (by depressing a button on the unit, for example) to discharge the 5 mL of test fluid. The initial flow of the fluid will complete the electrical circuit and start the timer. The timer will stop when the fluid has penetrated into the Reference Absorbent Pad and fallen below the level of the electrodes in the strikethrough plate.

Record the time indicated on the electronic timer.

Remove the test assembly and discard the used Reference Absorbent Pad. Rinse the electrodes with the 0.9% NaCl aqueous solution to "prime" them for the next test. Dry the depression above the electrodes and the back of the strikethrough plate, as well as wipe off the dispenser exit orifice and the bottom plate or table surface upon which the filter paper is laid.

Repeat this test procedure for a minimum of 3 replicates to ensure the strikethrough target of the Reference Absorbent Pad is met. If the target is not met, the Reference Absorbent Pad may be out of spec and should not be used.

After the Reference Absorbent Pad performance has been verified, nonwoven web samples may be tested.

Cut the required number of nonwoven web specimens. For web sampled off a roll, cut the samples into 10 cm by 10 cm sized square specimens. For web sampled off of a product, cut the samples into 15 by 15 mm square specimens. The fluid flows onto the nonwoven web specimen from the strike through plate. Touch the nonwoven web specimen only at the edge.

Neatly stack 5 plies of the Reference Absorbent Pad onto the base plate of the strikethrough tester.

Place the nonwoven web specimen on top of the 5 plies of filter paper. Two plies of the nonwoven web specimen are used in this test method. If the nonwoven web sample is sided (i.e., has a different layer configuration based on which side is facing in a particular direction), the side facing the wearer (for an absorbent product) faces upwards in the test.

Place the strikethrough plate over the nonwoven web specimen and ensure that the center of the strikethrough plate is over the center of the nonwoven web specimen. Center this assembly under the dispensing funnel.

Ensure that the upper assembly of the strikethrough tester is lowered to the pre-set stop point.

Ensure that the electrodes are connected to the timer. Turn the strikethrough tester "on" and zero the timer.

Run as described above.

Repeat this procedure for the required number of nonwoven web specimens. A minimum of 5 specimens of each different nonwoven web sample is required. The average value is the 32 mN/m low surface tension strikethrough time in seconds.

EXAMPLES 1-4

Spunbonded (S) single layer nonwoven fabrics were produced from 100-x wt % Ziegler-Natta polypropylene and x wt % of a hydrophobic melt additive (PPM17000 High Load Hydrophobic) and thermally bonded. The single S-layers had a weight of 20 g/m2. The contents of the hydrophobic additive in Examples 1-4 are summarized in Table 1.

TABLE 1

| Example | X [wt %] |
|---|---|
| 1 | 0 |
| 2 | 3 |
| 3 | 6 |
| 4 | 10 |

Examples 1-4 were tested for Low Surface Tension Strike Through (LST-ST). The results are summarized in Table 2.

TABLE 2

LST-ST

| | Example | | | |
|---|---|---|---|---|
| | 1 | 2 | 3 | 4 |
| | 5.20 | 14.13 | 8.25 | 10.22 |
| | 5.12 | 7.04 | 12.45 | 16.70 |
| | 4.27 | 6.97 | 11.93 | 9.84 |
| | 4.15 | 8.20 | 11.64 | 19.81 |
| | 4.80 | 7.41 | 14.13 | 12.64 |
| | 4.95 | 7.54 | 9.87 | 13.26 |
| | 3.80 | 7.53 | 10.16 | 11.41 |
| | 4.30 | 7.16 | 13.05 | 9.39 |
| | 4.66 | 8.68 | 9.25 | 20.75 |
| | 4.30 | 7.37 | 12.17 | 8.80 |
| | 5.08 | 6.98 | 10.32 | 10.40 |
| | 6.11 | 7.24 | 10.16 | 16.93 |
| | 4.74 | 7.89 | 11.65 | 14.83 |
| | 5.21 | 9.47 | 11.72 | 12.56 |
| | 6.25 | 8.58 | 11.19 | 16.33 |
| Average | 4.86 | 8.15 | 11.20 | 13.59 |
| Std. Dev | 0.68 | 1.81 | 1.53 | 3.81 |
| Min | 3.80 | 6.97 | 8.25 | 8.80 |
| Max | 6.25 | 14.13 | 14.13 | 20.75 |

EXAMPLE 5-7

Three S single layer nonwovens were produced from 100% Ziegler-Natta polypropylene and thermally bonded. The single S-layer had a weight of 20 g/m2. After the web making process of the nonwovens they were thermally treated with an in-line Omega Drying oven at 90° C., 120° C. and 135° C., for Example 5, 6 and 7, respectively.

EXAMPLE 8

An S single layer nonwoven was produced from 100% Ziegler-Natta polypropylene and thermally bonded. The single S-layer had a weight of 20 g/m2. After the web making process the nonwoven was thermally treated with an in-line IR-heater set to 65% power at the center and 60% at the edge of the nonwoven web.

EXAMPLE 9

An S single layer nonwoven was produced from 100% Ziegler-Natta polypropylene and thermally bonded. The single S-layer had a weight of 20 g/m2. After the web making process the nonwoven was thermally treated with an in-line Omega Drying oven at 120° C. Opposite Example 6, the through put had been decreased in the production of the material, resulting in a decreased line speed to increase the duration of the heat treatment. The resulting heat treatment of Example 9 was 15% longer than that of Example 6.

Table 3 below shows the resulting LST-ST measured on Example 5-9.

TABLE 3

| Example | | | | |
|---|---|---|---|---|
| 5 | 6 | 7 | 8 | 9 |
| 6.93 | 8.15 | 8.41 | 5.73 | 6.45 |
| 6.98 | 6.56 | 9.00 | 7.45 | 8.82 |
| 7.36 | 6.97 | 7.21 | 6.57 | 7.59 |
| 5.88 | 7.30 | 6.63 | 8.21 | 8.31 |
| 6.30 | 7.54 | 6.01 | 6.84 | 7.40 |
| 7.57 | 7.39 | 6.41 | 6.62 | 10.42 |

TABLE 3-continued

| | \multicolumn{5}{c}{Example} |
|---|---|---|---|---|---|
| | 5 | 6 | 7 | 8 | 9 |
| | 3.27 | 5.95 | 7.18 | 8.17 | 8.14 |
| | 6.30 | 6.31 | 6.83 | 6.46 | 6.99 |
| | 6.15 | 6.99 | 6.56 | 6.23 | 5.97 |
| | 5.96 | 8.25 | 6.03 | 6.60 | 7.97 |
| Average | 6.27 | 7.14 | 7.03 | 6.89 | 7.81 |
| Std. Dev | 1.21 | 0.74 | 0.98 | 0.81 | 1.26 |
| Min | 3.27 | 5.95 | 6.01 | 5.73 | 5.97 |
| Max | 7.57 | 8.25 | 9.00 | 8.21 | 10.42 |

EXAMPLES 10-13

Four S single layer nonwovens were produced from 90 wt % Ziegler-Natta polypropylene and 10 wt % of a hydrophobic melt additive (PPM17000 High Load Hydrophobic) and thermally bonded. The single S-layer had a weight of 20 g/m2. After the web making process of the nonwovens they were thermally treated with an in-line Omega Drying oven set to 90° C., 105° C., 120° C. and 135° C. for Example 10, 11, 12 and 13, respectively.

EXAMPLES 14-17

Four S single layer nonwovens were produced from 90 wt % Ziegler-Natta polypropylene and 10 wt % hydrophobic melt additive (PPM17000 High Load Hydrophobic) and thermally bonded. The single S-layer had a weight of 20 g/m2. After the web making process of the nonwovens they were thermally treated with an in-line IR-heater set to 50% power at the center and 45% at the edge of the nonwoven web, 60% power at the center and 55% at the edge of the nonwoven web, 65% power at the center and 50% at the edge of the nonwoven web, and 70% power at the center and 65% at the edge of the nonwoven web for Example 14, 15, 16 and 17, respectively.

EXAMPLE 18

An S single layer nonwoven was produced from 90 wt % Ziegler-Natta polypropylene and 10 wt % hydrophobic melt additive (PPM17000 High Load Hydrophobic) and thermally bonded. The single S-layer had a weight of 20 g/m2. After the web making process of the nonwoven it was thermally treated with an in-line IR-heater set to 65% power at the center and 60% at the edge of the nonwoven web, followed by heating in an Omega Drying oven at 120° C.

The hydrophobic additive content and heat treatment for Examples 10-18 are summarized in Table 4 below.

TABLE 4

| | Configuration | | |
|---|---|---|---|
| | S | | |
| | 20 g/m2 | | |
| Example | PPM17000 in S [%] | IR heater, center/edge [%] | Omega Drying oven temperature [° C.] |
| 10 | 10 | N/A | 90 |
| 11 | 10 | N/A | 105 |
| 12 | 10 | N/A | 120 |
| 13 | 10 | N/A | 135 |
| 14 | 10 | 50/45 | N/A |
| 15 | 10 | 60/55 | N/A |
| 16 | 10 | 65/60 | N/A |
| 17 | 10 | 70/65 | N/A |
| 18 | 10 | 65/60 | 120 |

LST-ST was measured on Example 10-18. The results are shown in Table 7.

TABLE 5

| | \multicolumn{9}{c}{Example} |
|---|---|---|---|---|---|---|---|---|---|
| | 10 | 11 | 12 | 13 | 14 | 15 | 16 | 17 | 18 |
| | 76.00 | 101.24 | 234.77 | 395.48 | 15.26 | 14.84 | 104.54 | 98.37 | 215.35 |
| | 61.97 | 49.95 | 276.72 | 657.52 | 17.00 | 12.71 | 152.30 | 111.38 | 110.34 |
| | 46.90 | 112.09 | 146.37 | 430.89 | 20.50 | 14.10 | 112.22 | 110.01 | 198.74 |
| | 74.91 | 88.00 | 273.29 | 474.56 | 19.56 | 28.91 | 266.32 | 98.23 | 410.14 |
| | 42.44 | 109.78 | 58.76 | 198.51 | 15.18 | 18.06 | 95.32 | 126.05 | 217.10 |
| | 79.87 | 142.88 | 305.67 | 494.47 | 22.90 | 19.65 | 156.70 | 55.01 | |
| | 38.29 | 40.85 | 140.77 | 538.19 | 11.38 | 15.53 | 304.52 | 64.02 | |
| | 67.46 | 37.91 | 196.46 | 380.06 | 18.17 | 20.92 | 138.70 | 113.62 | |
| | 35.59 | 93.40 | 51.80 | 609.90 | 24.31 | 25.86 | 301.90 | 70.28 | |
| | 65.22 | 213.77 | 178.43 | 437.63 | 19.12 | 16.57 | 211.70 | 74.74 | |
| | | | | | 20.24 | 16.76 | 270.70 | 52.05 | |
| | | | | | 16.97 | 19.58 | 317.12 | 86.01 | |
| | | | | | 36.15 | 30.45 | 216.29 | 33.97 | |
| | | | | | 12.96 | 30.45 | 273.13 | 76.24 | |
| | | | | | 19.00 | 14.05 | 408.33 | 96.01 | |
| Average | 58.87 | 98.99 | 186.30 | 461.72 | 19.25 | 19.90 | 221.99 | 84.40 | 230.33 |
| Std. Dev | 16.65 | 52.77 | 88.53 | 128.77 | 5.81 | 6.15 | 93.35 | 26.36 | 109.69 |
| Min | 35.59 | 37.91 | 51.80 | 198.51 | 11.38 | 12.71 | 95.32 | 33.97 | 110.34 |
| Max | 79.87 | 213.77 | 305.67 | 657.52 | 36.15 | 30.45 | 408.33 | 126.05 | 410.14 |

EXAMPLE 19

An S single layer nonwoven was produced from 90 wt % Ziegler-Natta polypropylene and 10 wt % hydrophobic melt additive (PPM17000 High Load Hydrophobic) and thermally bonded. The single S-layer had a weight of 20 g/m2.

Compared to Example 4, the temperature of the calender thermally bonding the nonwoven was increased with +10° C.

Table 6 below shows the LST-ST results from Example 19.

TABLE 6

| | LST ST [s] Example 19 |
|---|---|
| | 19.34 |
| | 14.72 |
| | 20.11 |
| | 14.50 |
| | 60.64 |
| | 15.93 |
| | 27.21 |
| | 18.45 |
| | 32.66 |
| | 46.12 |
| | 36.68 |
| | 16.23 |
| | 17.71 |
| | 26.82 |
| | 41.66 |
| Average | 27.25 |
| Std. dev. | 13.75 |
| Min | 14.50 |
| Max | 60.64 |

It can be see that when increasing the calender temperature with 10° C., the LST ST increases from 13.59 seconds (4) to 27.25 seconds (19).

EXAMPLE 20

An S single layer nonwoven was produced from 90% Ziegler-Natta polypropylene and 10 wt % of a hydrophobic melt additive (PPM17000 High Load Hydrophobic) and thermally bonded. The single S-layer had a weight of 20 g/m2. After the web making process the nonwoven was thermally treated with an in-line Omega Drying oven at 120° C. As Example 13, the through put had been decreased in the production of the material, resulting in a decreased line speed to increase the duration of the in-line heat treatment. The resulting heat treatment of Example 20 was 15% longer than that of Example 12 and comparable to the heat treatment of Example 6.

Table 7 below shows the LST-ST results from Example 20.

TABLE 7

| | LST ST [s] Example 20 |
|---|---|
| | 254.16 |
| | 342.97 |
| | 386.78 |
| | 134.31 |
| | 656.06 |
| Average | 354.86 |
| Std. dev. | 194.08 |
| Min | 134.31 |
| Max | 656.06 |

It can be seen that when increasing the heat treatment time with 15%, it increases the performance in terms of LST ST from 186.30 seconds (12) to 354.86 seconds (20).

EXAMPLE 21

A Spunbond single layer fabric was produced with bicomponent core/sheath configuration, consisting of 70 wt % core and 30 wt % sheath. The core comprised 100% Ziegler-Natta polypropylene. The sheath comprised 67 wt % Ziegler-Natta polypropylene and 33 wt % hydrophobic melt additive (PPM17000 High Load Hydrophobic). The nonwoven was thermally bonded. The single S-layer had a weight of 20 g/m2.

EXAMPLE 22-24

Spunbond single layer fabrics were produced with bicomponent core/sheath configuration, consisting of 70 wt % core and 30 wt %. The core comprised 100 wt % Ziegler-Natta polypropylene. The sheath comprised 100-X wt % Ziegler-Natta polypropylene and X wt % hydrophobic melt additive (PPM17000 High Load Hydrophobic). The nonwoven was thermally bonded. The single S-layer had a weight of 20 g/m2. After the web making process of the nonwovens they were thermally treated by an in-line IR-heater set to 65% power at the center and 50% at the edge of the nonwoven web.

The contents of the hydrophobic additive in the sheath of the fiber in Examples 22-24 are summarized in below Table 8.

TABLE 8

| Example | X [wt %] |
|---|---|
| 22 | 10 |
| 23 | 20 |
| 24 | 33 |

Table 9 below shows LST-ST results on Examples 21-24.

TABLE 9

| | Example | | | |
|---|---|---|---|---|
| | 21 | 22 | 23 | 24 |
| | 28.11 | 14.3 | 82.41 | 240.61 |
| | 17.14 | 13.56 | 43.19 | 273.30 |
| | 36.59 | 16.44 | 62.41 | 153.60 |
| | 12.35 | 15.81 | 72.28 | 147.92 |
| | 22.51 | 11.42 | 73.37 | 146.09 |
| | 41.57 | 10.70 | 117.86 | 502.41 |
| | 19.49 | 12.32 | 62.87 | 483.81 |
| | 25.87 | 12.74 | 110.75 | 262.96 |
| | 40.68 | 20.02 | 89.87 | 262.52 |
| | 30.65 | 14.95 | 91.99 | 370.45 |
| | 50.5 | 12.17 | 68.66 | 303.56 |
| | 10.03 | 16.71 | 51.44 | 249.07 |
| | 39.32 | 15.62 | 58.81 | 250.07 |
| | 20.28 | 13.28 | 94.30 | 354.30 |
| | 31.93 | 11.71 | 91.45 | 150.39 |
| Average | 28.47 | 14.12 | 78.11 | 276.74 |
| Std. Dev | 11.73 | 2.50 | 21.32 | 112.54 |
| Min | 10.03 | 10.70 | 43.19 | 146.09 |
| Max | 50.50 | 20.02 | 117.86 | 502.41 |

EXAMPLE 25

A spunbond single layer fabric was produced with bicomponent core/sheath configuration, consisting of 70 wt % core and 30 wt %. The core comprised 100 wt % Ziegler-Natta polypropylene. The sheath comprised 67 wt % propylene-based elastomer (consisting of approx. 15 wt % ethylene) and 33 wt % of a hydrophobic melt additive (PPM17000 High Load Hydrophobic). The nonwoven was thermally bonded. The single S-layer had a weight of 20 g/m2.

Table 10 below shows the LST-ST results on Example 25:

TABLE 10

|  | Example 25 |
|---|---|
|  | 136.81 |
|  | 77.96 |
|  | 134.97 |
|  | 74.01 |
|  | 118.13 |
|  | 57.90 |
|  | 38.32 |
|  | 132.20 |
|  | 138.89 |
|  | 94.23 |
| Average | 100.34 |
| Std. Dev | 36.86 |
| Min | 38.32 |
| Max | 138.89 |

Example 21 to Example 25 reveals an increase in LST-ST from 28.47 seconds to 100.34 seconds when substituting Ziegler-Natta polypropylene in the sheath of the bicomponent fiber with a propylene-based elastomer in the sheath of the bicomponent fiber.

EXAMPLE 26

A spunbond single layer fabric was produced was produced from 80 wt % Ziegler-Natta polypropylene, 10 wt % of a hydrophobic melt additive (PPM17000 High Load Hydrophobic), and 10 wt % of a Calcium Carbonate masterbatch (Fiberlink 201S). The fabric was thermally bonded. The single S-layer had a weight of 20 g/m2. After the web making process of the nonwoven it was thermally treated by an in-line IR-heater set to 65% power at the center and 60% at the edge of the nonwoven web followed by in-line heating in an Omega Drying oven at 120° C.

EXAMPLE 27

A spunbond single layer fabric was produced was produced from 90 wt % Ziegler-Natta polypropylene, and 10 wt % of Calcium Carbonate masterbatch (Fiberlink 201S) and thermally bonded. The single S-layer had a weight of 20 g/m2. After the web making process of the nonwoven it was thermally treated in an in-line Omega Drying oven at 120° C.

An overview of Example 26 and 27 is provided in Table 11 below.

TABLE 11

| | | | Configuration S 20 g/m2 | |
|---|---|---|---|---|
| Example | PPM17000 in S [%] | Fiberlink 201S [%] | Omega Drying oven temperature [° C.] | IR heater, center/edge [%] |
| 26 | 10 | 10 | 120 | 65/60 |
| 27 | 0 | 10 | 120 | N/A |

LST-ST results on Examples 26 and 27 are illustrated in Table 12 below.

TABLE 12

| | LST-ST [s] Example | |
|---|---|---|
| | 26 | 27 |
|  | 604.02 | 4.93 |
|  | 530.34 | 5.93 |
|  | 898.10 | 5.55 |
|  | 685.93 | 5.63 |
|  | 838.60 | 6.84 |
|  | 522.90 | 4.55 |
|  |  | 5.45 |
|  |  | 5.33 |
|  |  | 5.21 |
|  |  | 5.69 |
| Average | 679.98 | 5.51 |
| Std. dev. | 158.50 | 0.61 |
| Min | 522.90 | 4.55 |
| Max | 898.10 | 6.84 |

The LST-ST results reveal a LST ST of 5.51 seconds for Example 27, which shows that the presence of CaCO3 alone does not increase the LST-ST performance. The LST-ST of Example 26 compared to Example 18, reveals that the presence of CaCO3 and the applied heat treatments of the IR-heater and Omega Drying oven increases the LST ST from 230.33 seconds to 679.98 seconds. When comparing the state of the art of Example 4 to Example 26, the performance increases from 13.59 seconds to 679.98 seconds.

EXAMPLES 28-29

Two SMMS-multilayered nonwoven fabrics were produced from Ziegler-Natta polypropylene. The fabrics we added a hydrophobic additive (PPM17000 High Load Hydrophobic) to the various layers as described in Table 13. After the web making process of Example 29 the fabric was added a heat treatment with an in-line Omega Drying oven.

Table 13 gives an overview on material layup, additive content and heat treatment.

TABLE 13

| | Lay-up [g] | | | | Configuration | | |
|---|---|---|---|---|---|---|---|
| | S | M | M | S | SMMS | | |
| | 5.5 | 1 | 1 | 5.5 | 13 | | |
| Example | PPM17000 per beam [%] | | | | Total PPM17000 [%] | Omega Drying oven temperature [° C.] |
| 28 | 0 | 6 | 6 | 6 | 3.5 | N/A |
| 29 | 0 | 6 | 6 | 6 | 3.5 | 120 |

Examples 28-29 were tested for Low Surface Tension Strike Through (LST-ST). The results are summarized in Table 14.

TABLE 14

| | LST-ST [s] Example | |
|---|---|---|
| | 28 | 29 |
| | 18.35 | 23.99 |
| | 22.44 | 25.67 |
| | 21.70 | 28.36 |
| | 16.52 | 28.99 |
| | 23.13 | 30.71 |
| | 21.09 | 36.43 |
| | 24.01 | 33.29 |
| | 22.42 | 35.08 |
| | 21.30 | 30.98 |
| | 30.27 | 30.78 |
| | 28.86 | 31.71 |
| | 30.13 | 31.09 |
| | 17.95 | 29.27 |
| | 25.50 | 34.52 |
| | 28.48 | 31.24 |
| | 19.34 | 24.87 |
| | 25.11 | 32.50 |
| | 20.44 | 37.55 |
| | 27.07 | 34.13 |
| | 26.68 | 30.61 |
| | 27.65 | 33.90 |
| | 30.11 | 40.04 |
| | 17.50 | 32.49 |
| | 36.19 | 26.82 |
| | 30.73 | 27.60 |
| Average | 24.52 | 31.30 |
| Std. dev. | 5.03 | 4.70 |
| Min | 16.52 | 40.60 |
| Max | 36.19 | 59.50 |

TABLE 16

| | LST-ST [s] Example | | |
|---|---|---|---|
| | 30 | 31 | 32 |
| | 21.19 | 16.97 | 16.97 |
| | 33.40 | 22.91 | 22.91 |
| | 12.02 | 18.31 | 18.31 |
| | 22.27 | 22.74 | 22.74 |
| | 12.20 | 22.07 | 22.07 |
| | 24.97 | 28.60 | 37.35 |
| | 23.32 | 15.60 | 20.47 |
| | 26.33 | 44.03 | 33.25 |
| | 24.18 | 26.22 | 33.32 |
| | 16.26 | 20.00 | 37.67 |
| | 26.33 | 23.13 | 37.84 |
| | 20.08 | 29.65 | 29.83 |
| | 41.91 | 20.15 | 24.42 |
| | 47.98 | 20.91 | 43.57 |
| | 15.03 | 17.98 | 26.59 |
| | 13.90 | 17.99 | 42.61 |
| | 34.62 | 17.22 | 27.74 |
| | 25.18 | 12.88 | 22.61 |
| | 12.25 | 16.47 | 30.74 |
| | 32.08 | 18.53 | 35.16 |
| | 34.70 | 26.60 | 31.49 |
| | 13.69 | 21.61 | 43.26 |
| | 45.44 | 34.48 | 54.21 |
| | 21.81 | 14.35 | 35.09 |
| | 36.77 | 32.79 | 40.69 |
| Average | 25.52 | 22.49 | 31.64 |
| Min | 12.02 | 12.88 | 16.97 |
| Max | 47.98 | 44.03 | 54.21 |
| Std. dev. | 10.31 | 7.00 | 9.10 |

EXAMPLES 30-32

Three SS materials were produced with the spunbond fibers in both layers being bicomponent fibers of core/sheath configuration with a polyethylene sheath, accounting for 30 wt % of the total fiber, and polypropylene core, accounting for 70 wt % of the total fiber. A hydrophobic additive (PM16310) was added in 17% to the bicomponent's PE sheath of both of S layers for Examples 30-32. After the web making process of Example 31-32 the fabrics were added a heat treatment with an in-line Omega Drying oven of 100° C. and 120° C. for Example 31 and Example 32, respectively.

Table 15 gives an overview on material layup, additive content and heat treatment.

TABLE 15

| Lay-up [g] | | | | |
|---|---|---|---|---|
| S | | S | | |
| Core (PP) | Sheath (PE) | Core (PP) | Sheath (PE) | Configuration SS |
| 8.75 | 3.75 | 8.75 | 3.75 | 25 |

| Example | PPM17000 in sheath per beam [%] | Total PPM17000 [%] | Omega Drying oven temperature [° C.] |
|---|---|---|---|
| 30 | 17 | 5.1 | N/A |
| 31 | 17 | 5.1 | 100 |
| 32 | 17 | 5.1 | 120 |

Examples 30-32 were tested for Low Surface Tension Strike Through (LST-ST). The results are summarized in Table 16.

The invention claimed is:

1. A method for making a nonwoven fabric comprising:
   forming polymer fibers from a melt of the polymer material and using these fibers to obtain a nonwoven fabric during a subsequent nonwoven fabric formation procedure, wherein the polymer material comprises a thermoplastic polyolefin and wherein the melt of the polymer material comprises a melt additive which comprises a fatty acid ester derived from $C_{8-25}$ unsaturated or saturated carboxylic acids,
   thermal bonding at a temperature higher than 40° C. below the melting point of the polymer material and, additionally, one or both of the following steps:
   a. improving the mobility of the additive by including a filler having a higher thermal conductivity than the polymer material to the polymer material; and
   b. influencing the polymer crystallinity by including a nucleating agent, branched polymers and/or random co-polymers to the polymer material.

2. The method of claim 1, wherein the polymer material consists of or comprises a thermoplastic polymer.

3. The method of claim 1, wherein the filler has a thermal conductivity that is higher than the thermal conductivity of the polymer material by at least 0.2 $W \cdot m^{-1} \cdot K^{-1}$.

4. The method of claim 1, wherein the average particle size of the filler is 10 μm or smaller or wherein its thermal conductivity at room temperature is 1 $W \cdot m^{-1} \cdot K^{-1}$.

5. The method of claim 1, wherein the filler comprises $CaCO_3$ and preferably ground or precipitated $CaCO_3$.

6. The method of claim 1, wherein the nucleating agent comprises a nonitol, a trisamide, a sorbitol-based nucleating agent and/or an inorganic particulate having a particle size of 10 μm.

7. The method of claim 1, further comprising forming multicomponent polymer fibers from the melt of the one polymer material and a melt of another polymer material, wherein the other polymer material includes less or no additive, wherein at least the majority of the fiber surface is covered by the one polymer material and wherein thermal bonding is carried out at a temperature higher than 40° C. below the melting point of the lower melting polymer material.

8. The method of claim 7, wherein the multicomponent fiber is a bicomponent fiber or is of core-sheath configuration with the component going back to the one polymer material accounting for the sheath.

9. The method of claim 8, wherein the one and the other polymer material both are made of or comprise a thermoplastic polymer.

10. The method of claim 1, wherein the method comprises a continuous process for making a nonwoven fabric, where the fibers are continuously spun and directly dispersed on a carrier belt.

11. The method of claim 1, wherein the additive comprises a fatty acid ester derived from $C_{8-25}$, $C_{10-20}$ or $C_{14-18}$ unsaturated or saturated carboxylic acids.

12. A nonwoven fabric obtainable by the process of:
  forming polymer fibers from a melt of the polymer material and using these fibers to obtain a nonwoven fabric during a subsequent nonwoven fabric formation procedure, wherein the polymer material comprises a thermoplastic polyolefin and wherein the melt of the polymer material comprises a melt additive which comprises a fatty acid ester derived from $C_{8-25}$ unsaturated or saturated carboxylic acids,
  thermal bonding at a temperature higher than 40° C. below the melting point of the polymer material and, additionally, one or both of the following steps:
  improving the mobility of the additive by heat-treating the nonwoven fabric at 100° C. or more for 0.1 seconds or more after the nonwoven fabric formation procedure and/or including a filler having a higher thermal conductivity than the polymer material to the polymer material;
  influencing the polymer crystallinity by including a nucleating agent, branched polymers and/or random co-polymers to the polymer material,
  the fabric comprising polymer fibers where the melt additive is included in the polymer matrix, where the concentration of the melt additive is higher in a surface region than in a core region of the fibers and wherein the fibers comprise a rugged surface topography.

13. The method of claim 1, wherein the polymer material consists of or comprises of a polyolefin of at least one of polypropylene, polyethylene and Ethylene-Propylene copolymer or a combination of these.

14. The method of claim 1, wherein the average particle size of the filler is 1 μm or smaller and its thermal conductivity at room temperature is 2.0 $W \cdot m^{-1} \cdot K^{-1}$ or more.

15. The method of claim 1, wherein the nucleating agent comprises a nonitol, a trisamide, a sorbitol-based nucleating agent or an inorganic particulate having a particle size of 1 μm or smaller.

16. The method of claim 8, wherein the one and the other polymer material both are made of or comprise of at least one of a polyolefin, polyethylene and Ethylene-Propylene copolymer or a combination of these.

17. The method of claim 1, wherein the method comprises making a spunbonded or meltblown nonwoven fabric.

18. The method of claim 1, wherein the additive comprises a triglyceride.

19. A method for making a nonwoven fabric comprising:
  forming polymer fibers from a melt of the polymer material and using these fibers to form a nonwoven fabric, wherein the polymer material comprises a thermoplastic polyolefin, and wherein the melt of the polymer material comprises a melt additive which comprises a fatty acid ester derived from $C_{8-25}$ unsaturated or saturated carboxylic acids, thermal bonding at a temperature higher than 40° C. below the melting point of the polymer material;
  heat-treating the nonwoven fabric at 100° C. or more for 0.1 seconds or more after forming the nonwoven fabric to improve the mobility of the additive;
  adding a filler having a higher thermal conductivity than the polymer material to the polymer material; and
  adding a nucleating agent, branched polymers or random co-polymers to the polymer material to influence the polymer crystallinity.

20. The method of claim 1, further comprising heat-treating the nonwoven fabric in an additional step after the thermal bonding.

* * * * *